United States Patent
Rovison, Jr. et al.

(10) Patent No.: US 8,454,890 B2
(45) Date of Patent: Jun. 4, 2013

(54) PERACETIC ACID VAPOR STERILIZATION OF FOOD AND BEVERAGE CONTAINERS

(75) Inventors: John M. Rovison, Jr., Sanborn, NY (US); Charles J. Lymburner, Tonawanda, NY (US); Shibu Abraham, Stewartsville, NJ (US); Angela Thompson, East Amherst, NY (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 13/353,033

(22) Filed: Jan. 18, 2012

(65) Prior Publication Data

US 2012/0189494 A1 Jul. 26, 2012

Related U.S. Application Data

(60) Provisional application No. 61/434,515, filed on Jan. 20, 2011.

(51) Int. Cl.
*A61L 2/16* (2006.01)
(52) U.S. Cl.
USPC ............................................. 422/28

(58) Field of Classification Search
USPC ............................................. 422/28
See application file for complete search history.

(56) References Cited

U.S. PATENT DOCUMENTS

| 6,036,918 | A  | * | 3/2000 | Kowanko | 422/33 |
| 6,261,518 | B1 | * | 7/2001 | Caputo et al. | 422/22 |
| 6,536,188 | B1 |   | 3/2003 | Taggart | |
| 6,596,231 | B1 | * | 7/2003 | Catelli et al. | 422/28 |
| 6,790,380 | B2 | * | 9/2004 | Sato et al. | 252/186.23 |
| 6,945,013 | B2 |   | 9/2005 | Taggart | |
| 7,186,374 | B2 |   | 3/2007 | Zelina et al. | |
| 2010/0196197 | A1 | * | 8/2010 | Rovison et al. | 422/28 |

* cited by examiner

*Primary Examiner* — Sean E Conley
*Assistant Examiner* — Donald Spamer
(74) *Attorney, Agent, or Firm* — FMC Corporation

(57) ABSTRACT

The present invention is directed to a method of sterilizing a surface comprising treating such surface with a vapor comprising peracetic acid at a concentration of at least about 3500 ppm at between about 57° and about 75° C. Such method is preferably conducted in the absence of a hydrogen peroxide initiator, and is particularly suitable for the sterilization of polyethylene terephthalate bottles.

9 Claims, No Drawings

PERACETIC ACID VAPOR STERILIZATION OF FOOD AND BEVERAGE CONTAINERS

FIELD OF THE INVENTION

The present invention is directed to a method of sterilizing a surface comprising treating such surface with a vapor comprising peracetic acid at a concentration of at least about 3500 ppm at between about 57° and about 75° C.

BACKGROUND OF THE INVENTION

The use of plastic bottles composed of moldable plastics, such as polyethylene terephthalate (PET), has greatly expanded during the last few decades. Because such plastic bottles are almost unbreakable, weigh only about one-tenth the weight of glass, have excellent clarity and do not impart any taste to their contents, such bottles have become ubiquitous in today's society. As with all containers to be filled aseptically, plastic bottles must be functionally sterilized to remove trace contaminants such as bacteria (e.g. *C. botulinum*) or molds prior to being filled in order to attain aseptic filling and storage longevity requirements. Generally, containers are pre-produced and stored in bulk quantities until they are ready to be used and therefore are prone to contamination under normal storage conditions. Some plastic containers are stored as plastic tubes or plugs, and are blow molded with hot air prior to entering the filling machine; because of the low melt temperature of the plastic bottle, the inner surface is not necessarily sterilized during this blow molding step and requires additional treatment. Plastic bottles offer a unique challenge in that they cannot withstand the harsher treatments (time and temperature) that can be afforded to glass or metal containers in order to achieve sterility prior to filling. Accordingly, before these bottles can be filled with consumables, it is essential that they be sterilized in order to ensure that the risk of contamination by pathogenic microorganisms is minimized. Because of the vast number of such plastic bottles required to satisfy consumer demand, it is desirable that such sterilization be accomplished rapidly without any sacrifice in efficacy.

While peracetic acid (which is also called peroxyacetic acid) "PAA" is a known sterilizing agent, the prior art indicates that aqueous formulations of PAA are not suitable for the rapid sterilization of containers made out of PET. Thus, U.S. Pat. No. 6,790,380 discloses that in order to prevent the formation of harmful bacteria it is necessary to raise the temperature or concentration of a sterilizing agent, or to prolong a treating time. However, such publication indicates that none of these options are desirable for the sterilization of PET using aqueous PAA—heating the PAA solution tends to deform PET bottles; while raising the concentration results in undesirably high residues of hydrogen peroxide and/or acetic acid. Prolonging the treatment time is not desirable as this will slow down the process considerably.

U.S. Pat. Nos. 6,536,188 and 6,945,013 disclose the use of hydrogen peroxide fogs to disinfect the interior of PET bottles. These publications further indicate that oxonia (a mixture comprising 15-40 weight percent hydrogen peroxide; 7-13 weight percent acetic acid; and 5-10 weight percent PAA) may also be employed. However, these publications further indicate that it is necessary to first activate such sterilant and then to remove it using a plurality of drying stations.

United States Patent Application 2010/0196197 discloses the use of a true vapor (as opposed to a fog which contains suspended liquid particles) of a diluted PAA solution to sterilize surfaces. However, such publication indicates that such vapor should be employed at a temperature of between about 80 and about 120 degrees C., and for a contact time of between about 15 and 40 minutes. It is noted that the glass transition temperature of PET is about 75 degrees C., and that therefore PET bottles may deform at higher temperatures. Further, such an extended contact time is not amenable to the rapid sterilization of a large numbers of bottles.

Accordingly, it would be desirable if a method of rapidly sterilizing PET bottles employing PAA as the sterilant could be developed.

SUMMARY OF THE INVENTION

The present invention is directed to a method of sterilizing a surface comprising treating such surface with a vapor comprising peracetic acid at a concentration of at least about 3500 ppm at between about 57° and about 75° C. Such method is preferably conducted in the absence of a hydrogen peroxide initiator, and is particularly suitable for the sterilization of polyethylene terephthalate bottles.

DETAILED DESCRIPTION OF THE INVENTION

The present invention is directed to a method of sterilizing a surface comprising treating such surface with a vapor comprising peracetic acid at a concentration of at least about 3500 ppm at between about 57° and about 75° C.

As is employed herein, the term vapor intended to mean a state in which the peracetic acid is substantially entirely in the gaseous form. This is in contrast to mist or fog, both of which contain a significant proportion of liquid droplets suspended in the air.

Peracetic acid is typically employed in the form of an aqueous equilibrium mixture of acetic acid, hydrogen peroxide and peracetic acid, wherein the weight ratio of such components is about 35:10:15. Such composition may typically further comprise stabilizers such as phosphonic acids or phosphonates, i.e. Dequest® 2010 or sequestriants such as dipicolinic acid, as well as other ingredients such as: mineral acid catalysts (sulfuric, nitric, or phosphoric acids); surfactants such as anionic laurylates, sorbitans and their respective esters, i.e. polyethylene sorbitan monolaurylates; and short chain ($C_3$-$C_{12}$) fatty esters forming mixed peracids in solution.

Preferably, the method of this invention is conducted in the absence of a hydrogen peroxide activator (such as ultraviolet light) as it has been unexpectedly found that the activity of vapor phase PAA is reduced when such an activator is employed.

Prior to introduction into the heated gas stream, the peroxyacetic acid is preferably diluted, by the addition of water, to a concentration of at least about 3,500 parts per million (ppm). Although higher concentrations may be employed, it is preferred that the PAA has a concentration of below about 10,000 ppm, more preferably of below about 8,000 ppm in order to reduce the amount of peroxide or acetic residue that may remain on the treated surface. Most preferably, the PAA is diluted to a concentration of between about 3,750 and 4,250 ppm.

The heated gas stream is typically sterile air, although other gases such as nitrogen, $CO_2$, or inert noble gas carriers may also be employed. Such gas stream is typically heated to a temperature of at least about 300° C., preferably to a minimal temperature of about 250° C. and can be in excess of 350° C. providing it can be cooled sufficiently for application. The heated air is cooled to the desired temperature by the addition and flashing of the ambient temperature sterilizing solution.

In order to ensure that the peracetic acid is employed in a vapor form, it is preferable that the PAA solution is added to the heated gas stream at a rate which ensures that the stream is less than 100% saturated. Preferably, the PAA is added at a rate such that the heated gas stream is between about 75% and about 85% saturated. A saturation of about 80% can be achieved by adding the PAA solution at a rate of approximately 5 ml/minute (corresponding to about one drop per second) to a heated gas stream having an air flow rate of about 30 liters/minute.

The temperature of the vapor phase PAA stream is reduced to between about 57° and about 75° C.; the gas stream is then contacted with the material to be sterilized for a period of time sufficient to kill the contaminants of concern. This time period will vary according to variables such as the concentration of the peracetic acid vapor employed; the nature of the surface of the material to be sterilized; the particular contaminants to be sterilized; the concentration of the contaminants to be sterilized; and the like. However, it has been found that contact times as low as 5 seconds are sufficient to effectively sterilize test surfaces.

The process of the present invention is particularly suited for the sterilization of bottles and other containers made out of PET. However, a wide variety of other materials, including metals, glass, plastics, polymers, and elastomers may be sterilized employing the method of this invention.

The present method may be used to sterilize materials contaminated with those bacteria typically controlled by peracetic acid in the liquid form. These include bacteria and spores of the genus *Bacillus* using *B. thuringiensis* and *B. atrophaeus* as surrogates for more pathogenic species (forms) such as *C. botulinum* as well as more typical genera of bacteria, fungi, and viruses and protozoans often controlled by PAA such as (but not limited to): *Staphlococcus, Enterococcus, Salmonella, Campylobacter, Pseudomonas, Candida, Rhizopus, Mucor*, Influenza and the like.

The following Examples are presented to offer further illustration of the method of this invention, but are not intended to limit the scope of the invention in any manner.

EXAMPLES

Example 1

Construction of the Vaporization Apparatus

In order to prepare vaporized sterilant at various temperatures and concentrations, the following vaporization apparatus was constructed. A ½ inch diameter stainless steel tube was connected to a 100 psig compressed air supply. The tubing was connected to a stainless steel needle valve (for adjusting air flow) which was connected to a King Model 7910 Series Glass tube rotometer (0-40 Standard Liters per Minute) air flow meter. The air flow meter was connected to an electric heater having the capability to heat the air to 300 degrees F. (well above the boiling point of the peracetic acid solution) which was connected to a vaporizer box. This is a stainless steel box that has a glass window in the top for observation of the peracetic acid solution entry and vaporization. The vaporizer box was insulated on 5 sides to minimize heat loss. The bottom of the vaporizer box was placed on a laboratory hot plate from Biomega Research Products capable of heating the bottom of the box well above the boiling point of a PAA solution.

Another branch ½ inch stainless steel air tubing was used to pressurize a calibrated cylinder containing the various aqueous PAA or other sterilant solutions to be tested in the apparatus. The calibrated cylinder was connected to a ¼ inch stainless steel tube having a needle valve to control the flow of the solution through the tube. This tube was connected to the top of the vaporizer box such that drops of the sterilant solution exiting the tube would fall directly onto the heated bottom of the vaporizer box, permitting a sufficient heat input such that the solution would flash vaporize into the hot air stream. An insulated ½ inch stainless steel tube having a platinum thermocouple wire inserted therein (used to measure and control the temperature of the hot vapor stream) served as an outlet for the vaporized sterilant stream into the testing apparatus.

During the testing described below, the air flow rate of the heated air was set to 30 liters/minute by adjusting the King rotometer; and the needle valve was adjusted to provide the test solution at a rate of 5 mL/minute (approximately 1 drop/second); producing a hot vapor stream that was approximately 80% saturated. The temperatures of the electric heater was set to heat the air to 300° F.; and the hot plate temperature adjusted until the exiting vapor stream achieved the desired temperature indicated.

The strength of the diluted PAA/water mixtures employed was measured using a Metrohm 814 USB Sample Processor employing potentiometric evaluation of pH inflection points was used to determine the PAA content of the make-up solution.

Tests of Vapor Phase PAA in Sterilizing Containers

Evaluation of the efficacy of peracetic acid vapor at approximately 60° C. for approximately 5 and 10 seconds against *Bacillus atrophaeus* ATCC 9372 in beverage bottles The vaporizing apparatus described above was used to evaluate the efficacy of peracetic acid (PAA) vapor against spores of *B. atrophaeus* ATCC 9372, an endospore-forming bacteria used routinely as a sterilization test organism in beverage processing validation testing. The bottom surface of PET water bottles was inoculated with a prepared suspension of *B. atrophaeus* spores at a target of $10^5$ spores per bottle. The inoculated and dried bottles were exposed to vapor from a solution of various concentrations of PAA produced by the appropriate dilution of Clarity® peracetic acid (available from FMC Corporation) at about 60° C., for 5 and 10 seconds of exposure; with and without a five second treatment with ultraviolet light (a hydrogen peroxide activator) at the point of vapor delivery. The bottles were enumerated and plated on aerobic plate count ("APC"), and the remaining broth incubated for growth confirmation, as detailed below.

Inoculum Preparation

A prepared suspension of *B. atrophaeus* 9372 spores was purchased from Presque Isle Cultures. The solution contained 40% ethanol, and was stored in the laboratory refrigerator until the time of the test. The suspension contained $1.3 \times 10^{10}$ colony forming units of spores (CFU)/mL. A dilution was prepared in 40% ethanol for each test; the tests at 4,300 ppm of PAA contained approximately $1 \times 10^6$ spores/mL (target of $1 \times 10^4$ spores/bottle); and the tests at 2014 ppm and 7947 ppm contained approximately $1 \times 10^7$ spores/mL (target of $1 \times 10^5$ spores/bottle); to serve as the inoculum in the tests.

Bottle Carrier Preparation

Commercially available PET water bottles (0.5 L.) were emptied and rinsed with absolute ethanol, and allowed to dry overnight in a biological safety cabinet, in order to disinfect the inner surface. The bottles were then inoculated with 10 μL of the appropriate inoculum on the inner bottom surface with the working culture. They were then allowed to dry overnight in a biological safety cabinet until dry. The inoculated bottles were used for testing within one week of preparation.

Test Method

Inoculated bottles were placed onto the end of the vapor delivery hose in a fume hood located adjacent to the vaporizing apparatus, and subjected to the vapor for approximately 5 and 10 seconds of exposure, timed with a lab timer. Immediately following removal from the vapor delivery tube, 50 mL of a neutralizing broth comprising Letheen plus 0.5% sodium thiosulfate were added to the bottle using aseptic technique. The bottles were capped and shaken to ensure that any vapor which had condensed on the sides was mixed with the neutralizer. The bottles were then sonicated for 5 minutes, and vortex mixed for 30 seconds, followed by dilution in Butterfield's buffer and plating on APC. All test bottles with neutralizing broth, and all plates, were incubated at 35±2° C. for approximately 24 hours, prior to preliminary reading, and further incubated for several days to 2 weeks for final readings. The test was performed in singlet. Inoculum controls were performed in duplicate by enumerating inoculated and untreated bottles as described above. Upon completion of incubation, the bottles were evaluated for growth by means of turbidity. The results of such testing are summarized in Tables 1 and 2 below:

TABLE 1

Vapor test results using about 4000 ppm PAA solution

| PAA conc. in the cylinder | Time (s) | UV | Bottle growth | CFU remaining |
|---|---|---|---|---|
| 4,300 ppm* | 5 s. | Without | No | <50 |
| | 10 s. | | No | <50 |
| | 5 s. | With | Yes | <50 |
| | 10 s. | | Yes | <50 |
| NA (population controls) | 5 s. | NA | Yes | $2.25 \times 10^4$ |
| | 10 s. | | Yes | $8.5 \times 10^3$ |

*Determined using the autotitrator

TABLE 2

Vapor test results using a target of 2000 and 8000 ppm PAA solution

| PAA in cylinder (ppm)* | Time (s) | UV | Bottle growth | CFU remaining |
|---|---|---|---|---|
| 2014 ppm PAA | 5 s. | Without | Yes | $3.1 \times 10^4$ |
| | 5 s. | | Yes | $5.75 \times 10^3$ |
| | 10 s. | | Yes | $3.0 \times 10^4$ |
| | 5 s. | With | Yes | $6.45 \times 10^4$ |
| | 5 s. | | Yes | $2.95 \times 10^4$ |
| | 10 s. | | Yes | $2.2 \times 10^3$ |
| 7947 ppm PAA | 5 s. | Without | No | <50 |
| | 10 s. | | No | <50 |
| | 5 s. | With | Yes | ~50** |
| | 10 s.*** | | No | <50 |
| NA (populations controls) | 5 s. | NA | Yes | $2.9 \times 10^5$ |
| | 10 s. | | Yes | $1.455 \times 10^5$ |

*Determined using the autotitrator
**A result of 1 CFU plated from 50 mL, therefore approximately 50 CFU remaining
***This sample was tested for 5 seconds, then another 5 seconds shortly thereafter The above results demonstrate that substantially complete sterilization was observed by the use of PAA in concentrations of at least 4,300 ppm in the absence of ultraviolet light. These results are surprising given that UV light is a known activator of hydrogen peroxide.

Example 2

Residual Testing

Employing the vaporizing apparatus described in Example 1, tests were run in order to determine the amount of residual hydrogen peroxide left on the sterilized bottle surfaces. PET bottles (0.5 L.) were emptied and triple-rinsed with deionized water, then subjected to PAA vapor at concentrations of approximately 4000 and 14,000 ppm for 5 seconds. After such treatment, the bottles were filled with deionized water; and the water tested for low levels of hydrogen peroxide using a LaMotte HP-40 titration kit. A test of the amount of PAA delivered in the vapor was also conducted. For this purpose, high range PAA test strips were pre-wet with deionized water and placed in representative uninoculated bottles. The bottles were subjected to the vapor, and the test strip evaluated for color change to indicate the PAA present in the vapor. The results of such testing are summarized in Tables 3 and 4 below:

TABLE 3

Residual Hydrogen Peroxide Test Results using 0.5 L bottles, 5 second exposure

| | PAA solution concentration (ppm) | | Residual concentration after |
|---|---|---|---|
| Test | Target | Actual* | vaporous PAA treatment |
| LaMotte HP-40 | 4000 | 3943 | 0.3 to 0.4 ppm |
| | 14,000 | 13,973 | 2.0 ppm |

*measured using the autotitrator

TABLE 4

PAA Vapor Concentration using 0.5 L bottles, 5 second exposure

| | PAA solution concentration (ppm) | | Concentration applied in the vapor, using test strip to |
|---|---|---|---|
| Test | Target | Actual* | approximate |
| PAA Test strips | 4000 | 3943 | Approximately 250 ppm |
| | 14,000 | 13,973 | ≧1000 ppm (max. test strip) |

The above results indicate that the process of this invention can effectively sterilize PET bottles without leaving excess amounts of residual hydrogen peroxide.

Example 3

Evaluation of Control of *Bacillus subtillus* at Concentrations of 2000, 3000 and 4000 ppm of Vapor Phase PAA Employing the apparatus and process described in Example 1 vaporized PAA solutions having concentrations of 2000 ppm, 3000 ppm and 4000 ppm PAA were prepared by the dilution of Clarity® peracetic acid with deionized water as described below. Such testing involved treating the inoculated bottles with the vaporized PAA at about 60° C. for 5 seconds of exposure, with and without UV light treatment for 5 seconds.

Inoculum Preparation

A prepared suspension of *B. subtilis* 19659 spores was purchased from Presque Isle Cultures. The solution contained 40% ethanol, and was stored in a refrigerator until the time of the test. The suspension contained $1.6 \times 10^{10}$ CFU/mL of spores. A dilution was prepared in 40% ethanol for these tests, to target approximately $1 \times 10^8$ spores/mL (target of $1 \times 10^6$ spores/bottle) to serve as the inoculums in the tests.

Bottle Carrier Preparation

Commercially available PET water bottles (0.5 L) were emptied and inoculated with 10 μL of the appropriate inoculum on the inner bottom surface with the working culture. They were then allowed to dry overnight.

Biocide Preparation

Clarity® peracetic acid (available from FMC Corporation) was titrated using an autotitrator to determine the starting concentration, which were used to determine and prepare the dilutions necessary for solutions of PAA in deionized water. Biocide aliquots were prepared using 11.85 g Clarity® peracetic acid in 1 L water to obtain a 2000 ppm solution; 17.77 g Clarity® peracetic acid in 1 L deionized water to obtain a 3000 ppm solution and 23.70 g Clarity® peracetic acid in 1 L deionized water to make a 4000 ppm solution. A small amount of each solution was reserved for titration on the autotitrator, and the remainder added to the cylinder on the vapor apparatus. The results of such titration are shown in Table 5:

TABLE 5

Titration Results

| Target concentration | Autotitrator results (ppm) | Test temperature |
|---|---|---|
| 2000 ppm | 2053.67 | 58-60° C. |
| 3000 ppm | 3048.96 | 59.5° C. |
| 2000 ppm | 2080.69 | 56.0° C. |
| 3000 ppm | 3089.93 | 58.0° C. |
| 4000 ppm | 4204.76 | 57.0° C. |

*Starting concentration of PAA was 16.8808%

Test Method

Employing the apparatus and process described in Example 1, the inoculated bottles were treated with the vaporized PAA solution Immediately following removal from the vapor delivery tube, the bottles were either held for 5 seconds, or treated with UV light for 5 seconds Immediately following this step, 50 mL of a neutralizing broth Letheen plus 0.5% sodium thiosulfate was added to the bottle using aseptic technique. The bottles were capped and shaken to ensure that the vapor that had condensed on the sides was mixed with the neutralizer. The bottles were then sonicated for 5 minutes, and vortex mixed for 30 seconds, followed by dilution in Butterfield's buffer and plating on APC. All test bottles with neutralizing broth, and all plates, were incubated at 35±2° C. for approximately 24 to 72 hours, prior to preliminary reading, and further incubated for several days to 2 weeks for final readings. The tests were performed in duplicate. Inoculum controls were performed in duplicate as well, by enumerating inoculated and untreated bottles as described above. Upon completion of incubation, the bottles were evaluated for growth by means of turbidity.

Calculations $Log_{10}$Reduction=Average $log_{10}$(population control)−$log_{10}$(test sample)

The results of such testing are shown in Table 6 below.

TABLE 6

Vapor Test Results of 2000, 3000, and 4000 ppm PAA Solutions with and without Subsequent UV Treatment vs. *B. subtilis* Spores

| PAA in cylinder | UV treatment | Bottle growth | $Log_{10}$ CFU | Ave. $Log_{10}$ CFU | $Log_{10}$ Reduction |
|---|---|---|---|---|---|
| 2000 ppm | Yes | Neg. + | 5.08 5.18 | 5.13 | 1.23 |
|  | No | + + | 5.45 5.57 | 5.51 | 0.85 |
| 3000 ppm | Yes | Neg. Neg. | 4.24 4.83 | 4.53 | 1.82 |
|  | No | Neg. + | 4.92 5.32 | 5.12 | 1.23 |
| 4000 ppm | Yes | Neg. Neg. | 4.15 0.00 | 2.07 | 4.28 |
|  | No | Neg. Neg. | 0.00 0.00 | 0.00 | 6.35 |
| NA (pop. controls) | No | + + | 7.03 5.68 | 6.35 | NA |

The above results indicate that complete control was observed when PAA vapor having a concentration of 4000 ppm was employed in the absence of UV light. Substantially poorer control was observed by treatment with lower concentrations of PAA.

Example 4

Evaluation of the Efficacy of 35% Hydrogen Peroxide Vapor Compared with 4000 ppm PAA at Approximately 50, 55 and 60° C. Against *Bacillus Subtilis* ATCC 19659 in Beverage Bottles Treated for 5 Seconds Employing the apparatus and the process described in Example 1 (except as noted below), spores of *B. subtilis* 19659 were used to evaluate the efficacy of concentrated (approximately 35%) vapor phase hydrogen peroxide compared with vapor phase 4000 ppm peracetic acid (PAA) in PET beverage bottles at 50, 55 and 60° C. for 5 seconds of exposure.

Inoculum Preparation

A prepared suspension of *B. subtilis* 19659 spores was purchased from Presque Isle Cultures. The solution contained 40% ethanol, and comprised $1.6 \times 10^{10}$ CFU/mL of spores. A 1:100 dilution was prepared in 40% ethanol in order to target approximately $1 \times 10^8$ spores/mL, to serve as the working inoculum in this Example.

Bottle Carrier Preparation

Commercially available PET beverage bottles (0.5 L) were used in this test. The bottles were inoculated with 10 μL of the spore inoculum on the inner bottom surface with the working culture to target $1.6 \times 10^6$ spores/bottle. They were then allowed to dry overnight in a biological safety cabinet. The bottles were observed to be dry prior to testing.

Biocide Preparation

VigorOx® SP-15 peracetic acid (available from FMC Corporation) was titrated using the autotitrator to determine that the starting concentration was 15.2929%, which was used to determine and prepare the dilutions necessary for a solution of 4000 ppm PAA in deionized water. As a comparison, a sample bottle of Durox® hydrogen peroxide (comprising 35.7% hydrogen peroxide; available from FMC Corporation) was employed.

Test Method

Employing the vaporizing apparatus described in Example 1, formulations having the indicated temperatures were prepared. Inoculated bottles were placed onto the end of the vapor delivery hose, and subjected to the vapor for approximately 5 seconds of exposure, timed with a lab timer Immediately following removal from the vapor delivery tube, 50 mL of a neutralizing broth Letheen plus 0.5% sodium thiosulfate was added to the bottle using aseptic technique. An 100 uL aliquot of catalase (Worthington Biomedicals, 85,583 units per mgP, and 0.48 mgP/mL) was then added to each bottle to neutralize any remaining hydrogen peroxide. The bottles were capped and shaken to ensure that any vapor which had condensed on the sides was mixed with the neutralizer. The bottles were sonicated for 5 minutes, followed by vortex mixing for 30 seconds, then diluted in Butterfield's buffer and plated on Petrifilm APC. All test bottles with neutralizing broth, and all plates, were incubated at 35±2° C. for approximately 72 hours, prior to removal from the incubator to remain at room temperature for an additional 24 hours prior to counting. The test was performed in duplicate. Inoculum controls were performed in duplicate as well, by enumerating inoculated and untreated bottles as described above.

Calculations $Log_{10}$Reduction=Average $log_{10}$(population control)−$log_{10}$(test sample)

The results of such testing are summarized in Table 7 below:

TABLE 7

Vapor phase Hydrogen Peroxide and 4000 ppm PAA vs. bottles with 6.2 $log_{10}$ B. subtilis spores

| Product | Temperature | CFU/mL | $log_{10}$ CFU/mL | Ave. $log_{10}$ | Ave. $log_{10}$ reduction |
|---|---|---|---|---|---|
| 4000 ppm PAA | 50° C. | 23500 | 4.37 | 4.82 | 1.38 |
| | | 190000 | 5.28 | | |
| Hydrogen Peroxide | | 900000 | 5.95 | 5.86 | 0.35 |
| | | 570000 | 5.76 | | |
| 4000 ppm PAA | 55° C. | 64000 | 4.81 | 4.47 | 1.73 |
| | | 13500 | 4.13 | | |
| Hydrogen Peroxide | | 1400000 | 6.15 | 6.09 | 0.11 |
| | | 1100000 | 6.04 | | |
| 4000 ppm PAA | 60° C. | 0 | 0.00 | 0.00 | 6.20 |
| | | 0 | 0.00 | | |
| Hydrogen Peroxide | | 150000 | 5.18 | 5.18 | 1.03 |
| | | 150000 | 5.18 | | |
| Pop. Controls | RT | 1450000 | 6.16 | 6.20 | NA |
| | | 1750000 | 6.24 | | |

The above results indicate the process of the present invention will provide substantially complete sterilization of PET bottles; and that the use of hydrogen peroxide at such temperatures is relatively ineffective.

What is claimed is:

1. A method of sterilizing a surface comprising the steps of:
 (a) adding a peracetic acid solution to a heated gas stream to form a vapor phase peracetic acid stream; and
 (b) sterilizing said surface with said vapor phase peracetic acid stream wherein the peracetic acid is substantially entirely in the gaseous form with a concentration of between about 3500 ppm and about 10,000 ppm with a temperature between about 57° and about 75° C. wherein said sterilizing occurs for 5 to 10 seconds.

2. The method of claim 1 wherein said surface is composed of plastic.

3. The method of claim 1 wherein said surface is polyethylene terephthalate.

4. The method of claim 1 wherein said sterilizing is conducted in the absence of a hydrogen peroxide activator.

5. The method of claim 1 wherein the concentration of peracetic acid is at least about 3750 ppm.

6. The method of claim 5 wherein the concentration of peracetic acid is between about 3750 and about 4250 ppm.

7. The method of claim 1 wherein the vapor is less than 100% saturated.

8. The method of claim 7 wherein the saturation of the vapor is less than about 85%.

9. The method of claim 8 wherein the saturation of the vapor is between about 75% and about 85%.

* * * * *